United States Patent [19]

Schlosberg et al.

[11] Patent Number: 4,652,647

[45] Date of Patent: Mar. 24, 1987

[54] AROMATIC-METAL CHELATE COMPOSITIONS

[75] Inventors: Richard H. Schlosberg, Bridgewater; William N. Olmstead, Berkeley Heights, both of N.J.

[73] Assignee: Exxon Research and Engineering Company, Florham Park, N.J.

[21] Appl. No.: 772,462

[22] Filed: Sep. 4, 1985

Related U.S. Application Data

[63] Continuation-in-part of Ser. No. 686,449, Dec. 26, 1984, abandoned.

[51] Int. Cl.[4] ........................ C07F 5/00; C07F 7/00; C07F 9/00; C07F 11/00; C07F 13/00; C07F 15/02; C07F 15/04; C07F 15/06

[52] U.S. Cl. ........................................ 546/7; 546/10; 502/167; 502/168; 502/171

[58] Field of Search ........................ 502/167, 168, 171; 546/7, 10

[56] References Cited

U.S. PATENT DOCUMENTS

| | | | |
|---|---|---|---|
| 2,799,615 | 7/1957 | Heymons et al. | 546/7 X |
| 3,879,416 | 4/1975 | Kraus et al. | 502/167 X |
| 3,920,756 | 11/1975 | Tahara et al. | 502/167 X |
| 3,930,884 | 1/1976 | Zimmerman et al. | 502/167 X |
| 3,936,445 | 2/1976 | Pfitzner et al. | 502/167 X |
| 4,013,691 | 3/1977 | Mari et al. | 502/167 X |
| 4,292,435 | 9/1981 | Itani et al. | 546/10 X |
| 4,326,084 | 4/1982 | Druliner et al. | 502/167 X |
| 4,465,630 | 8/1984 | Akashi et al. | 502/167 X |

*Primary Examiner*—Patrick P. Garvin
*Attorney, Agent, or Firm*—Henry E. Naylor

[57] ABSTRACT

Disclosed are aromatic-metal chelate compositions which are deficient in hydrogen, are cross-linked, and which are comprised of two or more heteroatoms, wherein at least one of the heteroatoms are part of a 5 to 6 member heterocyclic ring, and wherein the metal constituent is selected from Groups III, IVB, VB, VIB, VIIB, and VIII of the Periodic Table of the Elements, and the heteroatom is selected from sulfur, oxygen, and nitrogen.

15 Claims, No Drawings

AROMATIC-METAL CHELATE COMPOSITIONS

CROSS REFERENCE TO RELATED APPLICATIONS

The application is a continuation-in-part application of U.S. Ser. No. 686,449 filed Dec. 26, 1984 and now abandoned.

BACKGROUND OF THE INVENTION

This invention relates to a new class of aromatic-metal chelate compositions which are characterized as being hydrogen deficient and cross-linked and containing two or more heteroatoms wherein at least one of the heteroatoms is part of a 5 or 6 member heterocyclic ring.

In the future, increasing amounts of the world's energy needs will be met by use of heavy liquid and solid hydrocarbonaceous materials. Although much of the world's energy needs will probably be met by burning these heavy hydrocarbonaceous materials in electric generating plants, a substantial portion of the world's energy needs will not be able to be supplied in the form of centrally generated electricity. One such need will be for transportation fuels, such as, gasoline, jet fuel, and diesel fuels. At some point in the future, a portion of these transportation fuels will have to be prepared from heavy hydrocarbonaceous raw materials. Even unexpected discoveries of large new field of conventional petroleum will only put off that point in the future by a number of years. As a result, much work is being done to develop economical methods for converting these heavy hydrocarbonaceous materials, which in most cases are highly contaminated, to light, clean, desirable products.

There are several approaches to the conversion of heavy hydrocarbonaceous materials to lighter products. One approach, and probably the oldest and most widely used, is simply pyrolysis, or coking. One drawback with coking is that a significant fraction of the feed is converted to gas and coke at the expense of potentially more valuable liquid products. While there is no problem in processing such heavy materials by coking, the yield of coke, in some cases, can amount to up to about 20 weight percent, or more. The coke is often of poor quality because of large amounts of heteroatom impurities.

Another approach is hydroconversion which offers the potential for substantially complete recovery of the heavy feed, including coke precursors, as valuable liquid products and/or good quality hydrocarbons for further upgrading. Despite strong liquid yield incentives, hydroconversion using conventional technology has not displaced coking because of the poor quality of these feeds and the consequent adverse effect on catalyst life expectancy. Compared to conventional light crude oils, these heavier materials are usually rich in high molecular weight, hydrogen lean, asphaltenic materials, which contain high concentrations of sulfur, nitrogen, and metal contaminants. Whereas coking simply rejects the worst of these objectionable materials in the coke phase, hydroconversion must cope with all of them to be successful. For example, rapid heterogeneous catalyst deactivation is a major problem owing to large asphaltenic molecules and deposition of the feed metal contaminants in the catalyst pores. Also, particulate matter contained in certain heavy feeds can lead to plugging of reactors.

Examples of conventional commercial processes for heavy feed upgrading include the so called H-Oil (Hydrocarbon Research Incorporated) and LC Fining (LUMMUS/Cities Service) processes. Both of these commercial processes suffer the limitation of catalyst deactivation by metal deposition.

Another commercial hydroconversion process which has met with limited success is the slurry process wherein the heavy feed is slurried using a finely divided catalyst, such as a vanadium sulfide catalyst.

One of the most promising hydroconversion technologies to be developed in recent years is the use of micron-size catalytic materials which comprise a metal sulfide component in a hydrocarbonaceous matrix. Such catalytic materials are generated in situ in the feeds at hydroconversion conditions from small amounts of certain oil souble or oil dispersible metal compounds. See U.S. Pat. Nos. 4,134,825; 4,266,742; and 4,244,839 all to Exxon Research and Engineering Company.

Although all of the above discussed processes have met with varying degrees of commercial success, there is still a pressing need in the art for the development of more economical methods, and more effective catalysts, for upgrading heavy hydrocarbonaceous materials.

SUMMARY OF THE INVENTION

In accordance with the present invention, there is provided a novel class of aromatic-metal chelate compositions which are hydrogen deficient, cross-linked, and contain two or more heteroatoms, wherein at least one of the heteroatoms is part of a 5 or 6 member heterocyclic ring. This new class of compositions is stable at hydroconversion conditions or decomposes to catalytically active forms at hydroconversion conditions.

The metal constituent of the compositions of the present invention is comprised of one or more metals selected from the group consisting of Groups III, IVB, VB, VIB, VIIB, and VIII of the Periodic Table of the Elements. The aromatic constituent contains moieties, each having two or more heteroatoms, wherein at least one of the heteroatoms is part of a 5 or 6 member heterocyclic ring. The heteroatoms are selected from the group consisting of sulfur, oxygen, and nitrogen, and are capable of forming a chelate with the metal constituent.

In preferred embodiments of the present invention, the metal constituent is a metal selected from groups VIB and VIII of the Periodic Table of the Elements and the aromatic constituent is a composition containing a heterocyclic ring wherein the heteroatom is nitrogen.

In other preferred embodiments of the present invention, the hydrogen deficient, cross-linked aromatic-metal chelate compositions are prepared by heating a mixture of the metal constituent and the aromatic constituent to a temperature from about 400° C. to about 550° C. for an effective amount of time.

In still other preferred embodiments of the present invention an aromatic-metal chelate is first formed by heating the metal constituent and the aromatic constituent to a temperature of about 300° C., followed by a second heating step wherein the aromatic-metal chelate is heated to a temperature from about 400° C. to 550° C., thereby causing the compositions to become hydrogen deficient and cross-linked.

DETAILED DESCRIPTION OF THE INVENTION

Below is a representive structure of the hydrogen-deficient cross-linked compositions of the present invention:

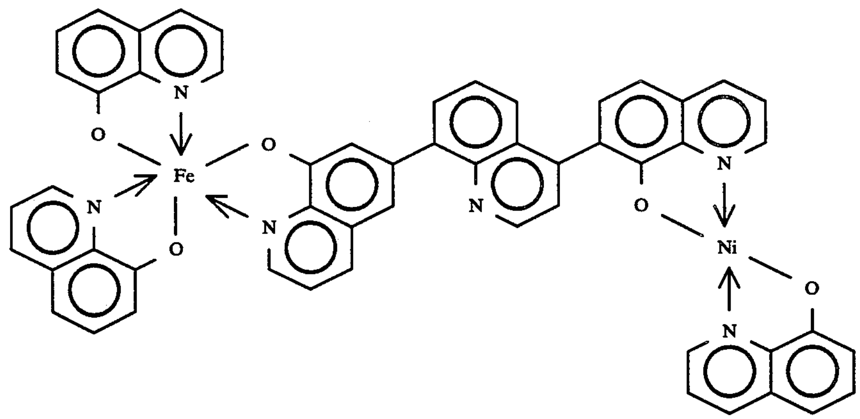

Aromatic metal chelate compositions of the prior art, such as those disclosed in U.S. Pat. Nos. 4,465,630; 3,879,416; 4,326,084; 4,013,691 and 3,920,756; differ from compositions of the present invention in that they are monomeric, that is, they are not cross-linked. Furthermore, they are not hydrogen deficient.

The compositions of the present invention are suitable for use as catalysts in a number of hydroconversion processes. The term "hydroconversion process" is intended herein to mean a process conducted in the presence of hydrogen in which a hydrocarbonaceous feed is either upgraded (refined) without substantial change in the boiling range of the oil, or a process in which the hydrocarbonaceous feed is converted to lower boiling products. Non-limiting examples of such processes include hydrogenation, hydrotreating, hydrosulfurization, hydrocracking, and reforming.

Operating conditions employed in hydroconversion processes in which the catalysts of the present invention are employed are well known in the art and, of course, will vary depending on the particular reaction desired. The following table summarizes typical reaction conditions in which the catalysts of the present invention may be utilized.

TABLE I

| Principal Reaction Desired | Temperature, °C. | Pressure, psig | Feed Rate V/V/HR | Hydrogen Rate SCF/bbl |
|---|---|---|---|---|
| Hydroreforming | 260–425 | 50–2000 | 0.1–10 | 500–10,000 |
| Hydrodesulfurization | 315–450 | 600–3500 | 0.05–5 | 300–20,000 |
| Hydrocracking | 230–450 | 200–2000 | 0.1–10 | 500–10,000 |

Suitable feedstocks for the hydroconversion processes of the present invention include hydrocarbonaceous oils derived from any suitable source such as petroleum, oil-shale, tar-sand, and coal. Typically, such feedstocks include naphthas, gas oils, atmospheric residua, vacuum residua, whole petroleum crude oils, including heavy crude oils, bitumen, kerogen, coal, etc.

The compositions of the present invention are hydrogen-deficient, cross-linked, aromatic-metal chelates wherein the metal constituent is one or more metals selected from the group consisting of Groups III, IVB, VB, VIB, VIIB, and VIII of the Periodic Table of the Elements, as illustrated in Lange's Handbook of Chemistry, Eleventh Edition, 1973. Preferred are metals selected from groups VB, VIB, VIIB, and VIII, and more preferred are metals selected from VIB and VIII, and most preferred are Fe, Co, and Ni. The metal constituent is chelated with an appropriate aromatic constituent by reacting the metal, in elemental form, or a precursor compound containing the metal, with the aromatic constituent, at a temperature from about 400° C. to about 550° C., preferably about 450° C., in an inert or hydrogen-containing atmosphere. For purposes of the present invention, a precursor compound is one which will allow the metal to be chelated by the aromatic constituent but will not adversely interfere with the catalytic activity of the resulting chelate. Nonlimiting examples of such precursor compounds include metal oxides and metal sulfides. If the chelate is formed at temperatures below 450° C., it is first heated to a temperature of about 450° C., with or without the hydrocarbon feed, to form a chelate which is stable at such temperatures, or which decomposes to catalytically active forms at such temperatures. Heating the chelate to a temperature of about 450° C. causes it to crosslink and become hydrogen deficient. By hydrogen deficient we mean that the cross-linked chelated composition has less hydrogen than the noncrosslinked chelate composition.

Aromatic compositions suitable for use herein are those compositions which contain two or more heteroatoms selected from the group consisting of sulfur, oxygen, and nitrogen, and which are capable of forming a chelate with the metal constituent. Preferred aromatic compositions are those which contain a heterocyclic ring wherein the heteroatom is nitrogen. Nonlimiting examples of such compositions include the 8-hydroxyquinolines, the 1,10-phenanthrolines, and benzo derivatives thereof. Preferred are the 8-hydroxyquinolines.

The relative amounts of aromatic composition and elemental metal or metal precursor, employed herein, is such that there is at least one organic ligand per metal atom when a metal precursor is employed, and there is at least enough organic ligand to fully complex with the metal when the elemental metal is employed.

The catalysts of the present invention have the unique advantages of (1) having the metal constituent dispersed on an atomic level, as opposed to a microcrystalline level, (2) potentially containing relatively inexpensive metals, such as iron, (3) being able to employ more active catalyst precursors, such as metal sulfides.

The following examples serve to more fully describe the manner of practicing the above-described invention as well as to set forth the best modes contemplated for carrying out various aspects of the invention. It is to be understood that these examples in no way serve to limit the true scope of this invention, but rather, are presented for illustrative purposes.

EXAMPLE 1

8-Hydroxyquinoline (10 g), having a molecular weight (MW) of 145, and carbon disulfide (0.09 g) were loaded into a 27 $cm^3$ 316 stainless steel reactor and pressurized with 500 psig of helium. The reactor and its contents were plunged into a preheated (450° C.) fluidized sand bath and held at that temperature for 30 minutes. The reactor contents were mixed by vertical agitation of the entire reactor. After cooling the reactor and its contents by plunging them into a water bath at room temperature (25° C.), the gases were vented and the solid contents were removed and washed with methylene chloride. The methylene chloride was removed by evaporation and other volatile compounds were removed by distillation at 250° C. and 0.2 torr. 8.6 g of non-volatile residue was recovered. Analysis revealed that metal from the walls of the reactor was incorporated into this residue: 68.3% C, 3.74% H, 8.6% N, 0.23% S, 8.2% O, 7.3% Fe, 1.94% Cr, 1.39% Ni, 0.22% Mo, 0.20% Mn.

The molecular weight of the nonvolatile residue was determined by vapor phase osmometry using orthodichlorobenzene. The average molecular weight of the soluble portion was about 4000. This evidences that the product was a cross-linked product because the molecular weight of a chelate comprising one Fe atom and three 8-hydroxyquinoline moieties has a molecular weight of 488. Furthermore, the ratio of hydrogen to carbon was found to be 0.65 on the final product versus 0.67 on the un-crosslinked material.

EXAMPLE 2

8-Hydroxyquinoline (3.61 g) and $Co_3O_4$ (1.50 g) were mixed and heated to 164° C. in a round bottomed flask. 1.00 g of the product solid was stirred with 10.0 g of toluene for 30 minutes. The suspension was filtered and the solid dried overnight at 110° C. 0.94 g of dried solid was recovered. Since this material was not heated to a temperature from about 400° to 550° C., it was be found to have the substantially same ratio of hydrogen to carbon (0.663) as the uncrosslinked material (0.667) and therefore it is not hydrogen deficient.

EXAMPLE 3

8-Hydroxyquinoline (2.40 g) and $Re_2O_7$ (2.00 g) were mixed, and heated to 200° C., in a round bottomed flask. 1.00 g of the product solid was stirred with 10.0 g of toluene for 30 minutes. The suspension was filtered and the solid dried overnight at 110° C. 0.92 g of dried solid was recovered. Since this material was not heated to a temperature from about 400° C. to 550° C., it was be found to have a ratio of hydrogen to carbon of 0.674 which evidences that it is not hydrogen deficient.

EXAMPLE 4

8-Hydroxyquinoline (8.00 g) and $MoO_3$ (2.00 g) were mixed, and heated to 200° C., in a round bottomed flask in about 30 minutes. The reaction mixture was then cooled and 8.67 g of solid product was recovered. Since this material was not heated to a temperature from about 400° C. to 550° C., it was found to have a ratio of hydrogen to carbon of 0.695 which evidences that it is not hydrogen deficient.

EXAMPLE 5

A mixture of 8-hydroxyquinoline and $MoO_3$ was mixed and sealed in a Pyrex tube. The tube was then placed in a 27 $cm^3$ 316 stainless steel reactor, and the reactor was plunged into a preheated (450° C.) fluidized sand both and held at that temperature for 15 minutes. The reactor contents were mixed by vertical agitation of the entire reactor. After cooling the reactor and its contents by plunging them into a water bath at room temperature (25° C.), the solid contents of the pyrex tube were removed. Analysis showed that the H/C ratio is 0.60, evidencing that the material is hydrogen deficient and therefore cross-linked.

The materials from Examples 1–4 were tested for their catalytic performance by the following procedure: each catalyst was placed into a small stainless steel batch autoclave (27 $cm^3$ of free space). A model compound mixture containing 1,2-diphenylethane, tetralin, naphthalene (except for Examples 11 and 12) and in some cases carbon disulfate was added to the catalysts. The autoclave in each example was closed and pressurized with hydrogen at 1000 psi for Examples 6–9 and Comparative Examples A and B and hydrogen at 500 psi for Examples 10–12 and Comparative Example C.

The autoclaves were plunged into a preheated (450° C.) fluidized sand bath. The autoclave reached the sandbath temperature within two minutes and was kept at that temperature for an additional 15 min. with moderate agitation, then rapidly quenched by plunging it into a water bath at room temperature. The reaction gases were collected and the liquid and solid contents of the autoclave were recovered by means of methylene chloride washings. In these systems we believe the following to be the functioning chemical transformations.

1. $C_6H_5CH_2CH_2C_6H_5 \xrightarrow{heat} 2C_6H_5CH_2.$

2. $C_6H_5CH_2. + H_2 \longrightarrow C_6H_5CH_3 + H.$

3. $C_6H_5CH_2CH_2C_6H_5 + H. \longrightarrow C_6H_5{-}H + C_6H_5CH_2CH_2.$

4. $C_6H_5CH_2CH_2. + H_2 \longrightarrow C_6H_5CH_2CH_3 + H.$

5. $2R. \longrightarrow R{-}R$

2′ $C_6H_5CH_2. +$ 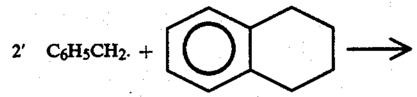 $\longrightarrow$ $C_6H_5CH_3 +$ 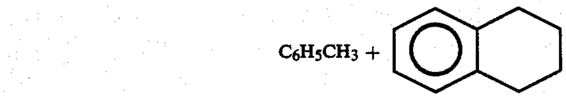.

2″ $C_6H_5CH_2. + \text{Catalyst}{-}H \longrightarrow C_6H_5CH_3 + \text{Catalyst.}$ As can be readily seen by examination of equations 2, 2′ and 2″, there are three pathways for toluene production. Only equation 2 leads to a secondary reaction pathway ultimately producing ethylbenzene and benzene. This chemistry was first reported by Vernon [Fuel 59, 102 (1980)] who demonstrated that the extent of benzene and ethylbenzene production (hydrogenolysis) is a function of total hydrogen pressure, and consequently H. concentration.

Capping the benzyl radicals with hydrogen from a catalyst or a donor molecule, such as tetralin, suppresses the deleterious radical chemistry pathways. Thus, in the model compound system, at constant hydrogen pressure, the better the donor the more effective the system is at replacing molecular hydrogen as a radical healer and the less ethylbenzene and benzene will be produced at constant toluene.

This chemistry parallels what happens in a heavy hydrocarbon hydroconversion system.

6. Heavy Hydrocarbon $\longrightarrow$ Radicals.

7. Radical. + $H_2$ $\longrightarrow$ Radical—H + H.

8. Heavy Hydrocarbon + H. $\longrightarrow$ Radical'. + R—H

9. Radical'. + $H_2$ $\longrightarrow$ Radical'—H + H.

10. Radical'. $\longrightarrow$ COKE

7' Radicals. + 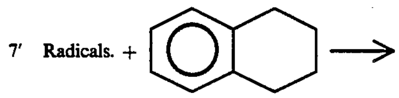 $\longrightarrow$

Radical—H + 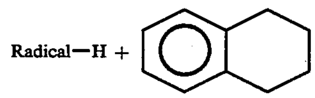.

7'' Radical. + catalyst—H $\longrightarrow$ Radical—H + catalyst.

COMPARATIVE EXAMPLES A AND B

Comparative Examples A and B (Table II) illustrate the parallel between the model compound system and heavy hydrocarbon hydroconversion chemistry. U.S. Pat. No. 4,134,825 discloses that an active metal component (e.g. molybdenum is combined with a carbonaceous component resulting in a catalytic material capable of suppressing coke formation (e.g. 10 above) in the hydroconversion of a petroleum residuum. Comparative Example A is the model compound-based experiment with no added catalyst. The extent of uninterrupted radical chemistry as maintained by the ratio of benzene plus ethylbenzene divided by toluene or twice the ethylbenzene divided by toluene (2EB/T) is 0.21±0.02. Comparative Example B is a duplicate of Comparative Example A with the addition of 200 ppm molybdenum as catalyst as described in U.S. Pat. No. 4,134,825. In Comparative Example B, the uninterrupted radical chemistry is reduced to a value of 2EB/T=0.16. Thus, the catalyst in Comparative Example B suppresses the pathway outlined in eq. 2–5 (model compound) and the analogous pathway leading to coke in the residua hydroconversion (eq. 7–10). By extension, a catalyst effective in suppression of coke during heavy hydrocarbon hydroconversion is effective in suppression of the radical chemistry leading to ethylbenzene from bibenzyl and vice versa. In both Comparative Examples A and B, carbon disulfide was added to insure complete sulfidation of the catalyst material.

EXAMPLES 6 AND 7

These examples are duplicates of Comparative Example A but using 200 ppm Re, as the rhenium chelate prepared in Example 3. In Example 6 the catalyst was introduced without the addition of carbon disulfide. This material was not effective for suppressing free radical chemistry as the ratio 2EB/T=0.23 is similar to the thermal blank. In Example 7, carbon disulfide was present. The resulting material was an effective catalyst (2EB/T=0.15).

EXAMPLES 8 AND 9

These examples employ 200 ppm cobalt as the chelate prepared in Example 3. Here, both with and without $CS_2$, the 2EB/T ratio is reduced to 0.14 and is indicative of an effective hydroconversion catalyst.

COMPARATIVE EXAMPLE C

This thermal blank example is a duplicate of Comparative Example A except that the hydrogen pressure is 500 psi instead of 1000 psi. Since eq. 2 shows that the amount of H formed is a function of $[H_2]$, with a lower $H_2$ pressure, less H will be produced and a reduced amount of benzene and ethylbenzene will be made. Thus, 2EB/T at 1000 psi>2EB/T at 500 psi. This is consistent with the results of Vernon [Fuel, 59, 102 (1980)].

EXAMPLE 10

Using 3000 ppm of the chelated metals as described in Example 1 produced a reduction in 2EB/T from 0.16 (Comparative Example C—thermal blank) to 0.094.

EXAMPLES 11 AND 12

Using 8000 ppm molybdenum as the chelate (Example 4) both with and without added $CS_2$ produced a diminished value of 2EB/T meaning that these, too, are effective hydroconversion catalysts.

TABLE II

| Example | Metal, ppm | Origin | $H_2$ Pressure psi at 20° C. | Bibenzyl, g | Naphthalene, g | Tetralin, g | Carbon Disulfide, g | 2 × Ethylbenzene / Toluene |
|---|---|---|---|---|---|---|---|---|
| Comp. Ex. A | — | — | 1000 | 6.00 | 1.50 | 1.37 | 0.15 | 0.21 + 0.02 |
| Comp. Ex. B | Mo, 200 | Microcat | 1000 | 6.00 | 1.50 | 1.50 | 0.15 | 0.16 |
| 6 | Re, 200 | Ex. 3 | 1000 | 6.00 | 1.50 | 1.52 | — | 0.23 |
| 7 | Re, 200 | Ex. 3 | 1000 | 6.00 | 1.50 | 1.50 | 0.16 | 0.15 |
| 8 | Co, 200 | Ex. 2 | 1000 | 6.00 | 1.50 | 1.52 | — | 0.14 |
| 9 | Co, 200 | Ex. 2 | 1000 | 6.00 | 1.50 | 1.50 | 0.16 | 0.14 |
| Comp. Ex. C | — | — | 500 | 6.00 | 1.50 | 1.41 | 0.16 | 0.16 |
| 10 | Fe+Cr+Ni+ Mo+Mn, 3000 | Ex. 1 | 500 | 6.00 | 1.50 | 1.44 | 0.16 | 0.094 |
| 11 | Mo, 8000 | Ex. 4 | 500 | 6.00 | — | 1.57 | — | 0.10 |

TABLE II-continued

| Example | Metal, ppm | Origin | $H_2$ Pressure psi at 20° C. | Bibenzyl, g | Naphthalene, g | Tetralin, g | Carbon Disulfide, g | 2 × Ethylbenzene Toluene |
|---|---|---|---|---|---|---|---|---|
| 12 | Mo, 8000 | Ex. 4 | 500 | 6.00 | — | 1.56 | 0.20 | 0.11 |

What is claimed is:

1. An aromatic-metal chelate composition which is deficient of hydrogen, cross-linked, and which is comprised of two or more heteroatoms, wherein at least one of the heteroatoms is part of a 5 or 6 member heterocyclic ring, and wherein the metal constituent is selected from Groups III, IVB, VB, VIB, VIIB, and VIII of the Periodic Table of the Elements, and the heteroatom is selected from sulfur, oxygen, and nitrogen.

2. The composition of claim 1 wherein the metal constituent is selected from groups VB, VIB, VIIB, and VIII of the Periodic Table of the Elements.

3. The composition of claim 2 wherein the metal constituent is selected from Fe, Co, and Ni.

4. The composition of claim 1 wherein the aromatic constituent contains a heterocyclic ring wherein the heteroatom is nitrogen.

5. The composition of claim 2 wherein the aromatic constituent contains a heterocyclic ring wherein the heteroatom is nitrogen.

6. The composition of claim 1 wherein the aromatic constituent is selected from 8-hydroxyquinolines, 1,10-phenanthrolines, and benzo derivatives thereof.

7. The composition of claim 5 wherein the aromatic constituent is selected from 8-hydroxyquinolines, 1,10-phenanthrolines, and benzo derivatives thereof.

8. The composition of claim 1 wherein the aromatic constituent is an 8-hydroxyquinoline.

9. The composition of claim 7 wherein the aromatic constituent is an 8-hydroxyquinoline.

10. The composition of claim 1 wherein the metal constituent is dispersed on an atomic level.

11. The composition of claim 9 wherein the metal constituent is dispersed on an atomic level.

12. A method for preparing hydrogen-deficient, cross-linked, aromatic-metal chelate compositions, which method comprises heating a mixture of the metal constituent and the aromatic constituent to a temperature from about 400° C. to about 550° C., for an effective amount of time, wherein the metal constituent is (a) a metal selected from Groups III, IVB, VB, VIB, VIIB, and VIII of the Periodic Table of the Elements, or (b) a precursor compound combining such metal, and wherein the aromatic constituent is an aromatic compound containing two or more heteroatoms selected from sulfur, oxygen, and nitrogen, and at least one of the heteroatoms is part of a 5 to 6 member heterocyclic ring.

13. The method of claim 12 wherein the metal constituent is selected from Fe, Ni, and Co.

14. The method of claim 13 wherein the one or more heteroatoms are nitrogen.

15. The method of claim 14 wherein the aromatic constituent is selected from the group consisting of the 8-hydroxyquinolines, the 1,10-phenanthrolines, and benzo derivatives thereof.

* * * * *